United States Patent [19]

Koshugi

[11] Patent Number: 4,666,861
[45] Date of Patent: May 19, 1987

[54] AQUEOUS SOLUTION AS AN ELUENT USED IN LIQUID CHROMATOGRAPHY

[75] Inventor: Junichi Koshugi, Matsudo, Japan

[73] Assignee: Kureha Kagaku Kogyo Kabushiki Kaisha, Tokyo, Japan

[21] Appl. No.: 795,275

[22] Filed: Nov. 5, 1985

Related U.S. Application Data

[62] Division of Ser. No. 517,956, Jul. 28, 1983, abandoned.

[30] Foreign Application Priority Data

Aug. 6, 1982 [JP] Japan ................. 57-136939
Aug. 31, 1982 [JP] Japan ................. 57-151275
Nov. 19, 1982 [JP] Japan ................. 57-203374
Nov. 19, 1982 [JP] Japan ................. 57-203375

[51] Int. Cl.$^4$ .......................................... A01N 30/02
[52] U.S. Cl. ................................. 436/161; 73/61.1 C
[58] Field of Search .............. 23/61.1 C; 252/408.1; 436/161, 162

[56] References Cited

FOREIGN PATENT DOCUMENTS 0061646 5/1981 Japan ................. 436/161

OTHER PUBLICATIONS

B. G. Belenkii et al, *Modern Liquid Chromatography of Macromolecules*, Journal of Chromatography Library, vol. 25, 1983, pp. 1, 2, 65-67.

Jeffrey R. Koup et al, *High-Performance Liquid Chromatographic Assay of Chloramphenicol in Serum*, Antimicrobial Agents and Chemotherapy, Sep. 1978, pp. 439-443.

Ronald E. Majors, *Techniques for Liquid Chromatographic Columns Packed with Small Porous Particles*, Analytical Chemistry, vol. 45, No. 4, Apr. 1973, pp. 755-762.

Kiyoshi Tsuji, *Fluorimetric Determination of Erythromycin and Erythromycin Ethylsuccinate in Serum by a High-Performance Liquid Chromatographic Post-Column, On-Stream Derivatization and Extraction Method*, Journal of Chromatography, 158 (1978) pp. 337-348.

Robert B. Hagel et al, *Stability-Indicating Assay for Mecillinam Using High-Pressure Liquid Chromatography*, Journal of Chromatology, 170 (1979).

D. Dell et al, The Liquid Chromatographic Analysis and Pharmacokinetics of the Semi-synthetic Cephalosporin 3-Methyl-7[4-(1,4,56-tetrahydro-2-pyrimidyl)-phenylacetamidol]-$\Delta^3$ Acid(1), from the Hoechst Pharmaceutical Research Laboratories, 1978, pp. 940-944.

Shigeaki Baba et al, *A Measurement of Individual Bile Acids in Serum by High-Performance Liquid Chromatography for Clinical Diagnostic Information of Hepatobiliary Diseases*, Kobe J. Med. Sci. 26, 89-99, Jun. 1980.

Primary Examiner—Charles Hart
Attorney, Agent, or Firm—Oblon, Fisher, Spivak, McClelland & Maier

[57] ABSTRACT

Disclosed is an aqueous solution as an eluent used in liquid chromatography for analysis of a specimen obtained from a human living body, comprising a mixture of acetonitrile and an aqueous solution of a member selected from the group consisting of acetic acid, a polybasic organic acid, a salt of organic acid and ammonium carbonate.

7 Claims, 38 Drawing Figures

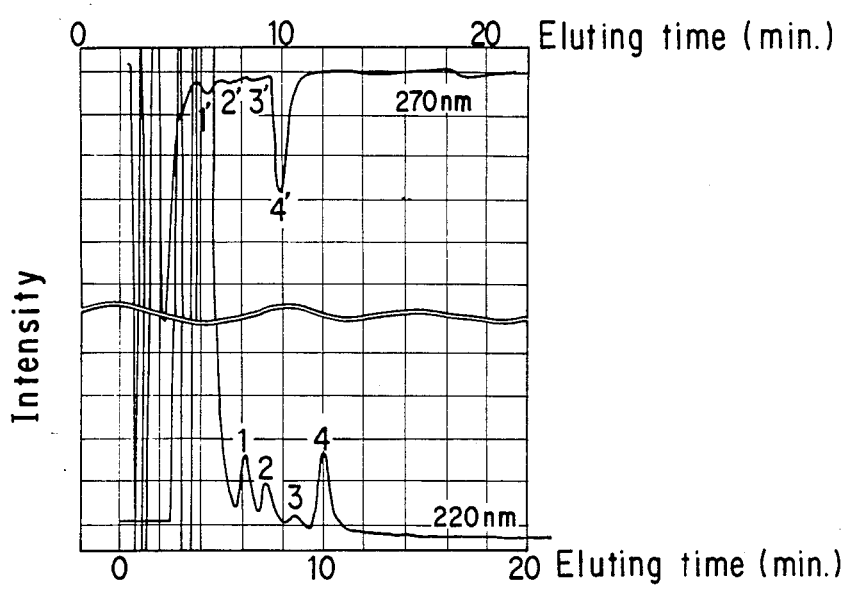
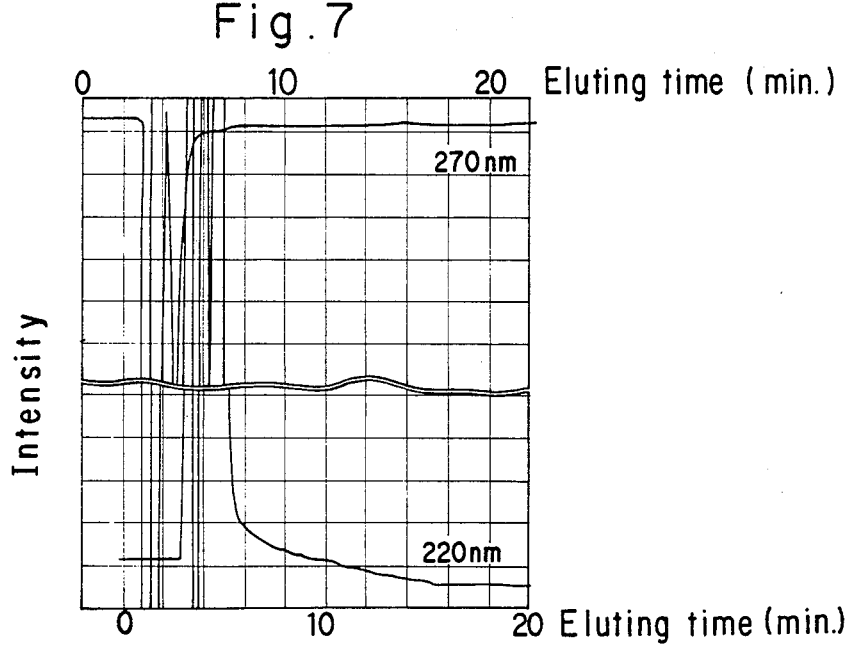

400">
AQUEOUS SOLUTION AS AN ELUENT USED IN LIQUID CHROMATOGRAPHY

This is a division of application Ser. No. 517,956, filed July 28, 1983, and now abandoned.

BACKGROUND OF THE INVENTION

The present invention relates to an aqueous solution as an eluent used in liquid chromatography for analysis of a specimen obtained from a human living body, comprising a mixture of acetonitrile and an aqueous solution of a member selected from the group consisting of acetic acid, a polybasic organic acid, a salt of organic acid and ammonium carbonate, and to a method for analyzing a specimen obtained from a human living body, comprising subjecting the specimen obtained therefrom to liquid chromatography while using, as an eluent, a mixture of acetonitrile and an aqueous solution of a member selected from acetic acid, a polybasic organic acid, a salt of organic acid and ammonium carbonate. More particularly, the present invention relates to an aqueous solution as eluent used in liquid chromatography for analysis of a specimen obtained from a human living body in order to detect a specific peak or a specific peak pattern intercorrelating to the hepatic morbid state, comprising a mixture of acetonitrile and an aqueous solution of a member selected from the group consisting of acetic acid, a polybasic organic acid, a salt of organic acid and ammonium carbonate, the volume ratio of acetonitrile to said aqueous solution of acetic acid or ammonium carbonate being 5:95 to 25:75, preferably 5:95 to 15:85, and the volume ratio of acetonitrile to said aqueous solution of the polybasic organic acid or the salt of organic acid being 1:99 to 25:75, preferably 5:95 to 15:85, and to a method for analysing a specimen obtained from a human living body in order to detecting a specific peak or specific peak pattern intercorrelating to the hepatic morbid state, comprising subjecting the specimen obtained therefrom to liquid chromatography while using, as an eluent, a mixture of acetonitrile and an aqueous solution of a member selected from acetic acid, a polybasic organic acid, a salt of organic acid and ammonium carbonate, the volume ratio of acetonitrile to said aqueous solution of acetic acid or ammonium carbonate is 5:95 to 25:75, preferably 5:95 to 15:85, and the volume ratio of acetonitrile to said aqueous solution of the polybasic organic acid or the salt of organic acid is 1:99 to 25:75, preferably 5:95 to 15:85.

It is extremely important for the diagnosis and treatment of a disease of a patient to analyze the components and the properties of a specimen such as blood, plasma, serum, cerebrospinal fluid, urine etc. taken from the patient and to obtain the information(s) concerning the morbid state of the patient based on the thus obtained analytical data. Such informations have been hitherto obtained by subjecting such a specimen to various chemical or biochemical analytical means, however, for the purpose of elucidating the various morbid states in various cases or seizing the more exact morbid state, the development of analytical methods by which more accurate informations are available has been demanded.

Particularly, in the cases of hepatic diseases and nephrotic diseases, because of the complicated morbid states thereof, the analytical methods which can provide new indices closely related to the morbid states of hepatic diseases and nephrotic diseases have been demanded.

As the conventional index of the morbid states of the hepatic diseases, the activity values of enzymes in the living body, for instance, GOT(glutamic-oxaloacetic transaminase), GPT(glutamic-pyruvic transaminase), LDH (lactic acid dehydrogenase), LAP(leucine aminopeptidase), etc., the biochemical analytical values of the blood components such as protein, lipoprotein, neutral fat, bilirubin, cholesterol etc. may be used.

However, it is difficult to trace precisely the change of the morbid state of a hepatic disease which causes the generation of very complicated factors in the patient suffering from the hepatic disease only by the utilization of the values obtained by the chemical analyses and biochemical analyses.

Accordingly, a new trial for diagnosing the morbid state of hepatic diseases while utilizing antigen-antibody reaction has been carried out (refer to Gastr., 76, 665(1979)), and it was reported that chronic active hepatitis and chronic inactive hepatitis or liver cirrhosis can be diagnosed at the respective probabilities of 50 to 60% and 20 to 40%, however, the method is complicated in its operations and is not satisfactory from the viewpoint of the accuracy in judging.

On the other hand, utilization of liquid chromatography is now attracting attention. Liquid chromatography is one of the analytical techniques based on the principles different from those on which the chemical or biochemical analytical method stands.

Utilization of liquid chromatography in the medical and clinical fields has been greatly expected in principle from the viewpoints that even the thermally and/or chemically unstable substances can be isolated and detected by liquid chromatography without being denaturated and that liquid chromatography is able to analyse many components in one operation while using a relatively minute amount of specimen, and a number of trials have been carried out in utilizing liquid chromatography.

However, in general, the peaks or the peak pattern in the chromatogram obtained by liquid chromatography are different to each other case by case where the eluents are different, and it changes according to the mode of combination of the eluent and the specimen, and accordingly, it is difficult to seize the peak, which directly correlates to the morbid state in a chromatogram. Particularly, in hepatic diseases, a method by which the morbid state of each of the various hepatic diseases including chronic hepatitis, liver cirrhosis etc. can be traced has not been established.

As a result of the present inventor's studies for the object of finding a method of clinical analysis of the specimen obtained from the patient suffering from a hepatic disease, in which an extremely small amount of the specimen is subjected to liquid chromatography, thereby obtaining a fraction exhibiting a peak which correlates to the progress of morbid state or the degree of seriousness of the disease within a short time period in a simple manner and quantifying the peak to examine the change of the morbid state from the change of the thus quantified peak appearing in the fractions, the present inventor has found a method fulfilling the object, and has attained the present invention.

SUMMARY OF THE INVENTION

In a first aspect of the present invention, there is provided an aqueous solution as an eluent used in liquid chromatography for analysis of a specimen obtained from a human living body, comprising a mixture of acetonitrile and an aqueous solution of a member selected from the group consisting of acetic acid, a polybasic organic acid, a salt of organic acid and ammonium carbonate.

In a second aspect of the present invention, there is provided a method for analyzing a specimen obtained from a human living body, comprising subjecting the specimen obtained therefrom to liquid chromatography while using, as an eluent, a mixture of acetonitrile and an aqueous solution of a member selected from acetic acid, a polybasic organic acid, a salt of organic acid and ammonium carbonate.

BRIEF EXPLANATION OF DRAWING

In FIG. 2, K-1 denotes healthy person, K-2 denotes patient suffering from acute hepatitis, K-3 denotes patient suffering from chronic hepatitis, K-4 denotes patient suffering from liver cirrhosis, K-5 denotes patient suffering from a complication of liver cirrhosis and encephalosis K-6 denotes patient suffering from a complication of liver cirrhosis and hepatoma, K-7 denotes patient suffering from a complication of liver cirrhosis, hepatoma and encephalosis, K-8 denotes patient suffering from fatty liver, K-9 denotes patient suffering from lupoid hepatitis, K-10 denotes patient suffering from cholestasis, and K-11 denotes patient suffering from primary biliary cirrhosis. In each of FIGS. 8-1 to 8-10, respective abscissas show elution time (min.).

DETAILED DESCRIPTION OF THE INVENTION

Figure 1A:
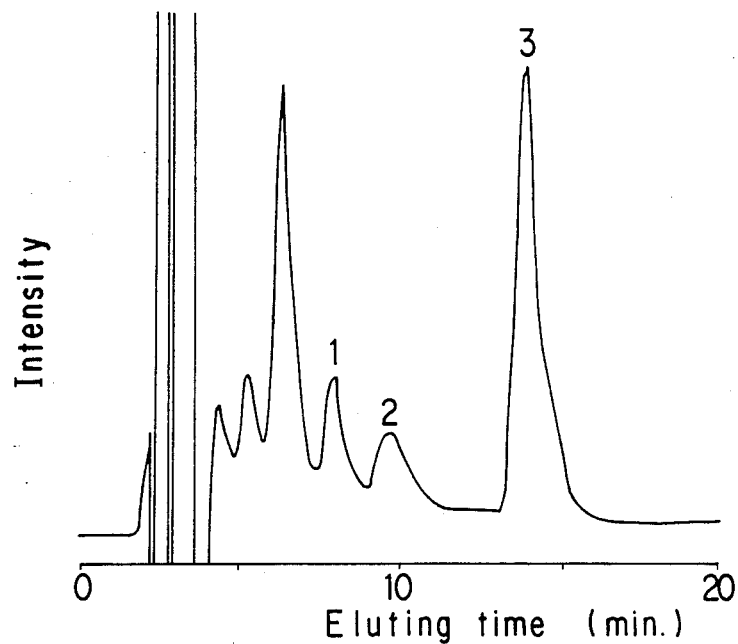
FIGS. 1A and 1B, FIGS. 3A, 3B, 3C and 3D, FIGS. 4A, 4B, 4C and 4D and FIGS. 20A and 20B are the respective chromatographic pattern of the human sera.

The method for analyzing of the present invention comprises the steps of subjecting a specimen obtained from a human living body to liquid chromatography to analyze the specimen, to detect a specific peak or a specific peak pattern in a fractions obtained from the specimen by the use of a mixture, as an eluent, of acetonitrile and an aqueous solution of a member selected from the group consisting of acetic acid, a polybasic organic acid, a salt of organic acid and ammonium carbonate, and to use the thus detected peak or peak pattern as an index of the morbid state of a hepatic disease such as acute hepatitis, chronic hepatitis, liver cirrhosis, hepatoma, fulminant hepatitis, lupoid hepatitis, cholestasis, primary biliary cirrhosis, liver fibrosis, etc.

According to the present invention, the peak inter-correlating to the hepatic morbid state is sharply formed and detected within 30 min of subjecting the specimen to liquid chromatography about 10 microliters of a specimen such as plasma, serum, cerebrospinal fluid, lymph, ascitic fluid, bile or urine as it is or the deproteinized specimen, and a hepatic disease can be diagnosed at a probability of almost 90 to 100% by the method according to the present invention.

According to the present invention, chronic hepatitis, liver cirrhosis of which no abnormality could have been detected from the test value on hepatic function such as GOT, GPT etc. can be detected as the respective peaks. For instance, while the conventional test value shows a reduction with the aggravation of the morbid state from acute hepatitis to liver cirrhosis, the peak according to the present invention shows an increase in its intensity (as the area of the peak or the height of the peak).

In addition, it has been recognized that the peak according to the present invention shows the increase of its intensity with the appearance of the sign of aggravation of liver cirrhosis, for instance, disturbance of consciousness, appearance of ascitic fluid, retention of ascitic fluid, etc., the aggravation of liver cirrhosis hitherto having been difficult to quantify From these facts, the present invention is an extremely useful means and provides new informations concerning the morbid state of hepatic diseases.

The packing material used in the present invention may be those commercialized as the packing material for high-speed liquid chromatography, and among them, the silane-treated packing material derived from silica is preferable. Such a packing material can be obtained by a known method, for instance, by treating pulverized silica with a silane compound. The column prepared by filling the packing material is set to a commercialized liquid chromatographic apparatus or an optional apparatus provided with the same function as above and is placed at the service of analyzing the specimen taken from a human living body.

The specimen obtained from a human living body is used as it is, is used after pre-treating with a known de-proteining reagent such as methanol, trichloroacetic acid, perchloric acid, etc. or is used after removal of high-molecular weight protein by a membrane for ultra-filtration (it is possible to operate the chromatographic apparatus by providing an apparatus for removing the high-molecular substances in front of the column). However, in order to improve the life of the packing material, the stability of the column (frequently hindered by clogging) and the analytical accuracy, the specimen is preferably pretreated for removal of proteins.

The eluent used in the present invention is a mixture of acetonitrile and an aqueous solution of a member selected from the group consisting of acetic acid, a polybasic organic acid, a salt of organic acid and ammonium carbonate. The volume ratio of acetonitrile to the aqueous solution of acetic acid or ammonium carbonate in the mixture as the eluent is 5:95 to 25:75, preferably 5:95 to 15:85, and the volume ratio of acetonitrile to the aqueous solution of the polybasic organic acid or the salt of organic acid in the mixture as the eluent is 1:99 to 25:75, preferably 5:95 to 15:85. The concentration of acetic acid is 0.01 to 1.0% by weight, preferably 0.1 to 0.5% by weight, and the concentration of ammonium carbonate in the aqueous solution of ammonium carbonate is 0.1 to 10% by weight, preferably 0.3 to 3.0% by weight.

Further, the concentration of the polybasic organic acid is 0.01 to 1.0% by weight, preferably 0.1 to 0.5% by weight, and the concentration of the salt of organic acid in the aqueous solution of the salt of organic acid is 0.01 to 10% by weight preferably 0.1 to 5.0% by weight. The salt of an organic acid is used after dissolving in distilled water or water treated by an ion-exchanging resin.

As the salt of an organic acid, sodium salt, potassium salt, magnesium salt and ammonium salt of monobasic acid such as formic acid, acetic acid, propionic acid etc., those salts of dibasic acid such as oxalic acid, succinic acid etc. and those salts of tribasic acid such as citric acid, etc. may be used, and as polybasic organic acid, dibasic acid such as oxalic acid, succinic acid etc. and tribasic acid such as citric acid etc. may be used. Of course, an aqueous solution of the acid may be used after neutralizing with a basic substance such as sodium hydroxide, potassium hydroxide etc., and the salt may be a mixture of more than two salts.

In addition, in the elution, the amount of acetonitrile relates to both the eluting speed of the components of the specimen for analysis and the separating efficiency of the peaks in chromatogram, and the concentration of the salt of an organic acid therein relates to the separation of the peaks.

Furthermore, the eluent may be used after being added with an antiseptic such as sodium azide etc.

The thus prepared eluent according to the present invention does not have a bad influence upon the packing material, and does not cause the clogging of the column even in the case of a specimen containing basic, acidic or amphoteric substance in a large amount, and makes the stabilized determination possible.

The liquid chromatography is carried out at a temperature generally in a range of 5° to 40° C. with the specimen in an amount of about 5 to 20 microlitres.

In the case where the eluent is the mixture of acetonitrile and the aqueous solution of salt of organic acid or polybasic organic acid, the separated fractions are detected by an ultra violet light in a range of 200 to 280 nm, for instance, 270 nm to find out the peak, and for seizing the relationship to the morbid state more precisely, for instance, it is preferable to detect the peak by using two light waves, for instance, 220 and 270 nm. Also, in the case where the eluent is the mixture of acetonitrile and the aqueous solution of acetic acid, the separate fractions are detected by an ultra violet light in a range of 200 ,to 280 nm, and for seizing the relationship to the morbit state more precisely, for instance, it is preferable to detect the peak by using two light waves, for instance, 220 and 270 nm. Further, in the case where the eluent is the mixture of acetonitrile and the aqueous solution of ammonium carbonate, the separated fractions are detected by an ultra violet light in the rage of 200 to 280 nm, it is preferable to detect the peak by using two light waves, for instance, 220 and 270 nm.

In the case where the eluent is a mixture of acetonitrile and the aqueous solution of acetic acid, salt of organic acid or acetic acid, when fluorescent analysis is carried out, a light 220 to 360 nm is used for excitation and a fluorescence of 280 to 520 nm, preferably, a light of 320 to 350 nm is used for excitation and a fluorescent light of 450 to 470 nm is used.

The present invention is not only utilizable to the clinical analysis but also utilizable to the analysis of the components of specimens taken from the living body, for instance, by packing a larger column with the carrier (packing material, in other word, the filler) to fractionally collect the component showing the peak(s).

The present invention will be explained more in detail while referring to the following non-limitative examples:

EXAMPLE 1

After packing a stainless-steel column of 4 mm in diameter and 30 cm in length with a commercialized packing material ($\mu$-Bondapak® phenyl, 10 micrometers in particle diameter, made by Waters Co.), the thus packed column was set to a high-speed liquid chromatographic apparatus provided with a UV-detector and a mixture of acetonitrile and an aqueous 0.1% solution of sodium oxalate (volume ratio of acetonitrile to aqueous solution of 10:90) was poured into the thus packed column at a rate of 1.0 ml/min to stabilize the UV-detector and the recorder.

Into 500 microliters of a serum obtained from a healthy person or of a serum taken from a patient of complication of liver cirrhosis and encephalosis, 5 microliters of methanol was added, and after mixing them, the mixture was kept in a warm water bath at 60° C. for 20 min to coagulate the proteinic components. Thereafter, the thus treated mixture was subjected to centrifugal separation at 5° C. for 20 min and at 3000 G to collect the supernatant liquid, which was dried to solid and dissolved in 500 microliters of methanol to obtain the specimen to be examined.

Each 10 microliters of the thus prepared specimens was poured into the column of the high-speed liquid chromatographic apparatus to carry out the analysis under a UV-light of 270 nm at a sensitivity of 0.02.

Figure 1B:
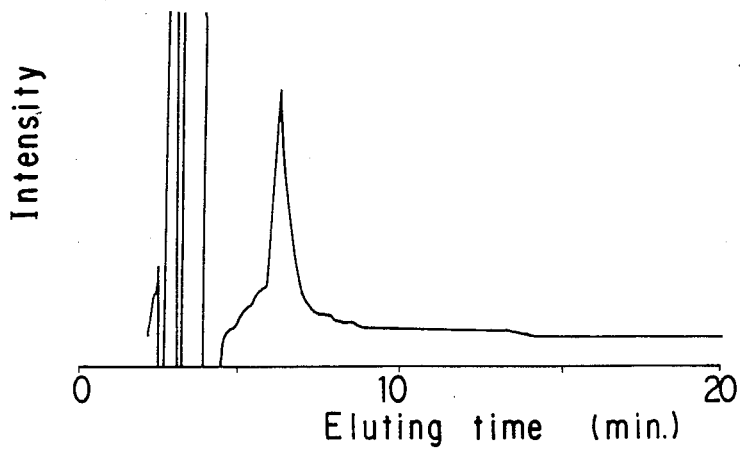

As a result of analysis for 20 min, the respective chromatograms, one for the healthy person shown in FIG. 1B and the other for the patient shown in FIG. 1A were obtained. In FIG. 1A, three unusual peaks 1, 2 and 3 were observed, which were not observed in FIG. 1B of the serum of the healthy person.

EXAMPLE 2

The respective sera taken from 51 patients suffering from various liver diseases were analyzed by high-speed liquid chromatography under the same conditions as in Example 1 and the results are shown in Table 1.

TABLE 1

| Hepatic disease | Total number of patients | Number of patients showing the specific peaks | Rate of detection (%) |
|---|---|---|---|
| Acute hepatitis | 3 | 3 | 100 |
| Chronic hepatitis | 11 | 11 | 100 |
| Lupoid hepatitis | 2 | 2 | 100 |
| Cirrhosis | 20 | 20 | 100 |
| C+ with hepatoma | 2 | 2 | 100 |
| C+ with c.c.++ | 5 | 5 | 100 |
| C+ with hepatoma and c.c.++ | 2 | 2 | 100 |
| (Cirrhosis in total) | 29 | 29 | 100 |
| Primary choleic cirrhosis | 3 | 3 | 100 |
| Cholestasis | 3 | 3 | 100 |
| (total) | 51 | 51 | 100 |

Notes:
C+ means cirrhosis
c.c.++ means encephalosis

As seen in Table 1, all the serumal specimens obtained from patients suffering from at least one hepatic disease showed at leat one specific unusual peak in the chromatographic pattern, the specific unusual peak being not observed in the chromatographic patern of the serum takne from healthy person.

Figure 2:
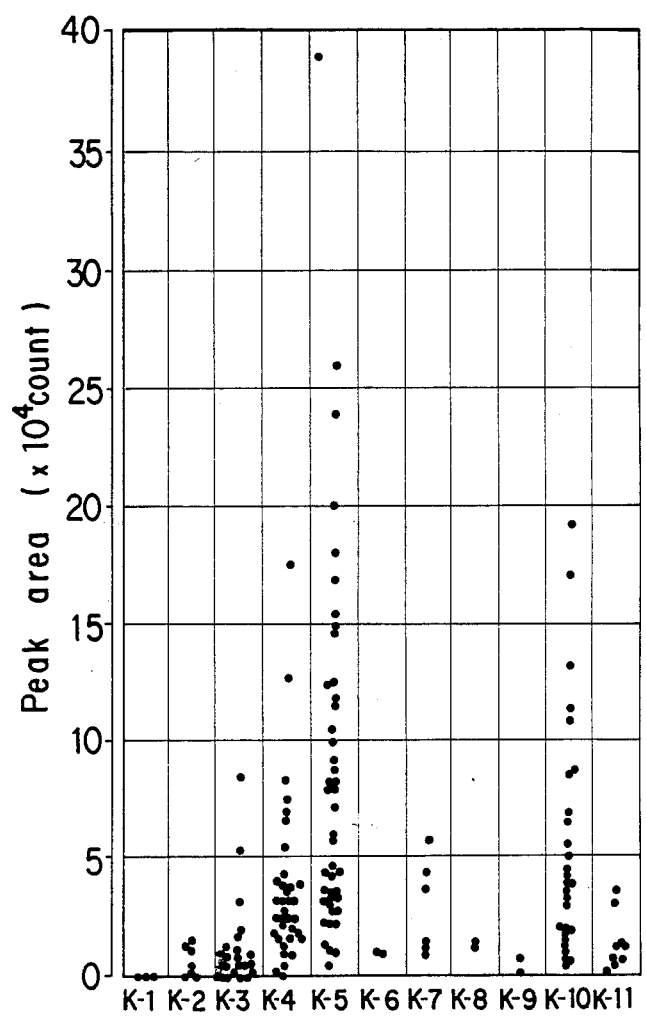
FIG. 2 is the area of the respective peaks corresponding to various hepatic diseases.

In addition, in the case where the patients were classified concerning the appearance and the insensity (area or height) of one of the specific unusual peaks, Peak No. 3 including the changes of the patients' morbid states, a result shown in FIG. 2 was obtained.

In FIG. 2, when the peak area was compared between the respective patient group, for instance those of acute hepatitis, those of chronic hepatitis, liver cirrhosis and liver cirrhosis with encephalosis, it is noticed that the peak area depends on the morbid state of the patients. Particularly, in the patient suffering from liver cirrhosis with a complication of encephalosis, the peak showed a specifically large area.

EXAMPLE 3

A plasma obtained from a patient suffering from cholestasis and treated as in Example 1 was subjected to highspeed chromatographic analysis in the same apparatus as in Example 1 under the same conditions as in Example 1 except for using a mixture of acetonitrile and an aqueous 0.1% solution of sodium acetate (volume ratio of 10:90), a mixture of acetonitrile and an aqueous 0.1% solution of trisodium citrate (volume ratio of 10:90) or a mixture of acetonitrile and an aqueous 0.1% solution of sodium succinate instead of the mixture of acetonitrile and an aqueous 0.1% solution of sodium oxalate in Example 1. As a result, in every case, unusual peak(s) was observed in the chromatogram, which has never been observed in the plasma of healthy persons.

EXAMPLE 4

The same serum specimen as in Example 1 was divided into the two equal portions, and one of the portion was directly subjected to the high speed liquid chromatography under the same conditions as in Example 1, and the other portion was subjected to de-proteinization and subsequently subjected to the high speed liquid chromatography as above. The de-proteinization was carried as follows:

After mixing the serum specimen with an aqueous 5% solution of trichloroacetic acid at a volume ratio of 1:1, the mixture was centifuged to precipitate the insoluble matter in the mixture, and the supernatant liquid was used for chromatography.

As the result, both the thus treated specimen and the not-treated serum itself gave the respective chromatographic patterns and in each of the two patterns, unusual peak was recognized. Such peak did not appear in both the chromatographic patterns obtained from the un-treated serum and from the treated serum (de-proteinized) taken from a healthy person.

The above-mentioned test was carried out under the different conditions of the high speed liquid chromatography while using a mixture of acetonitrile and an aqueous 0.1% solution of citric acid (volume ratio of 10:90) instead of the mixture of acetonitrile and an aqueous 0.1% solution of sodium oxalate as in Example 1.

The results were the same as above. Namely, the specific unusual peaks appeared in both the chromatographic pattern on the de-proteinized serum of the patient and the chromatographic pattern on the not-deproteinized serum of the patient. Such peak did not appear in both the chromatographic pattern on the de-proteinized serum of the healthy person and the chromatographic pattern on the not-de-proteinized serum of the healthy person.

The result of the present Example is useful in simplifying the test procedures in the method according to the present invention.

EXAMPLE 5

Figure 3A:
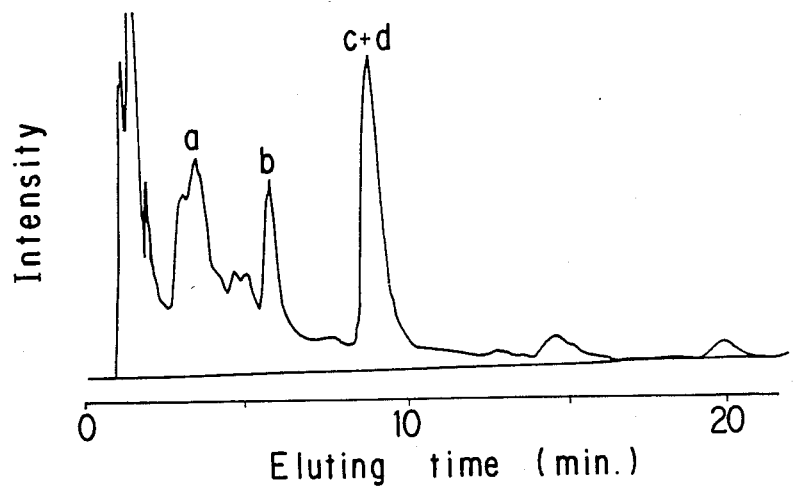
Figure 3B:
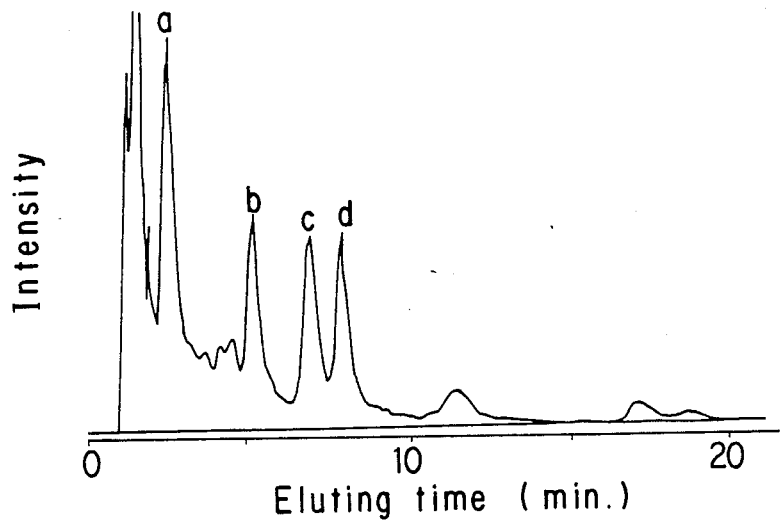
Figure 3C:
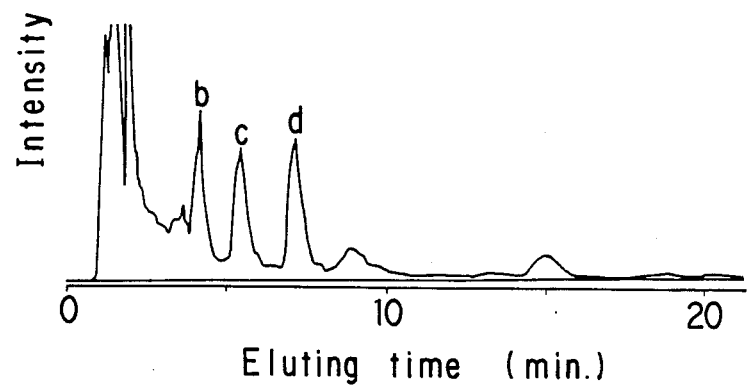
Figure 3D:
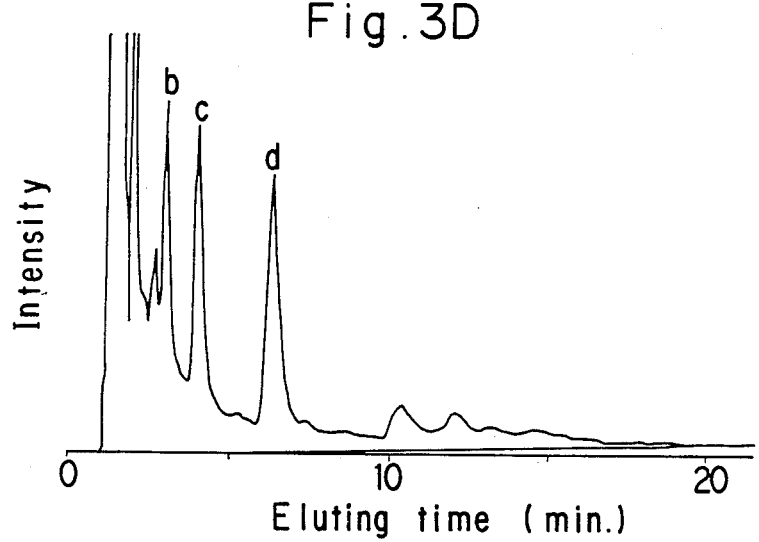
Figure 4A:
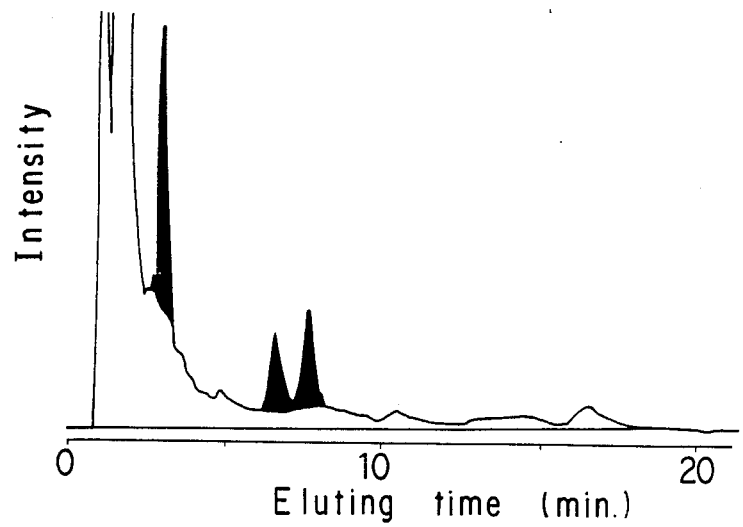
Figure 4B:
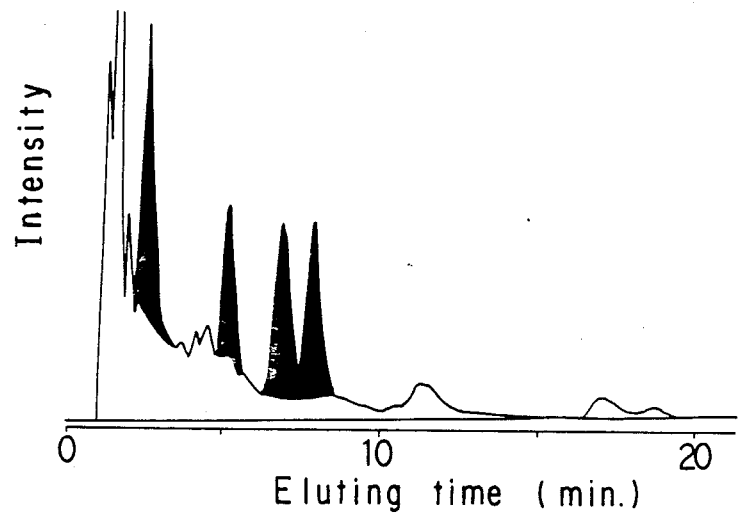
Figure 4C:
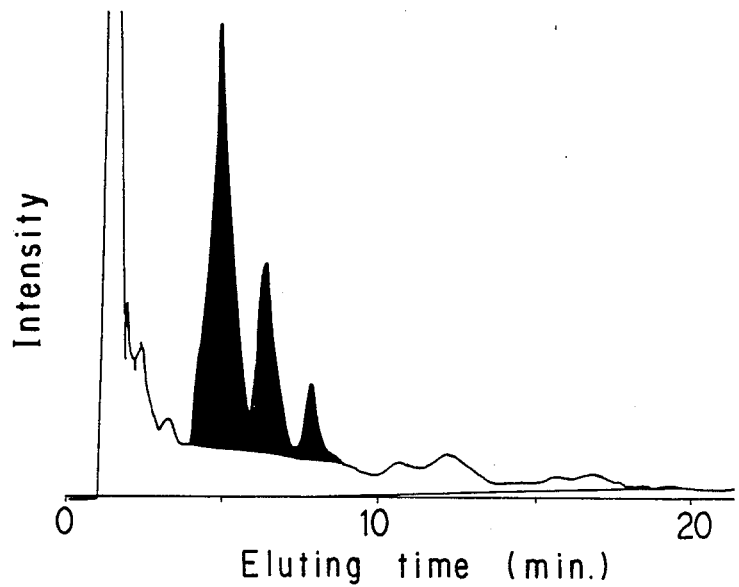
Figure 4D:
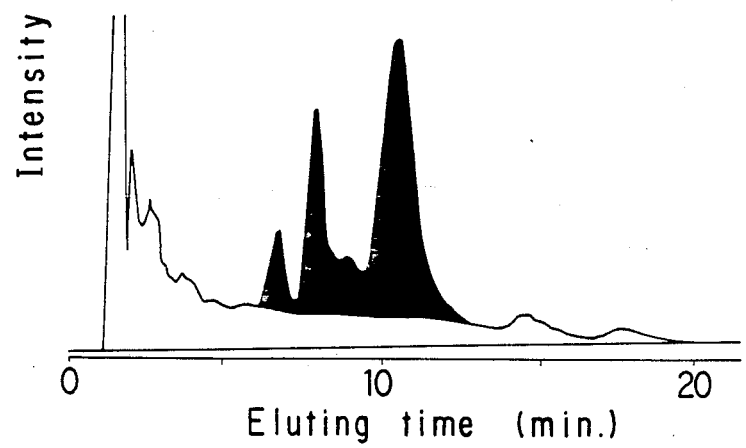

A serum obtained from a patient suffering from acute liver failure or a serum taken from a healthy person was subjected to high-speed liquid chromatography while using the same apparatus used in Example 1 except for using a fluorescence monitor (made by HITACHI Works) at $\lambda$ex of 220 nm and $\lambda$em of larger than 340 nm, under the same conditions as in Example 1 except for using a mixture of acetonitrile and an aqueous 0.3% solution of sodium acetate (volume ratio of 10:90) shown in FIG. 3A, a mixture of acetonitrile and the aqueous 0.3% solution of sodium acetate (volume ratio of 11.25:88.75) shown in FIG. 3B, a mixture of acetonitrile and the aqueous 0.3% solution of sodium acetate (volume ratio of 12.5:87.5) shown in FIG. 3C or a mixture of acetonitrile and the aqueous 0.3% solution of sodium acetate (volume ratio of 15:85) at a flow rate of 2.0 ml/min instead of the mixture of acetonitrile and the aqueous solution at the flow rate of 1.0 ml/min in Example 1. The results are shown in FIGS. 3A to 3D. As seen in FIGS. 3A to 3D, at least 4 unusual peaks are observed in every chromatogram of the serum of the patient, however, almost any one of such unusual peak could not observed in the chromatogram of the healthy person's serum. In addition it was found that the volume ratio of acetonitrile to the aqueous solution of sodium acetate (0.3%) may have a correlation to the number of peaks in the chromatogram under the specified conditions.

EXAMPLE 6

The same serum of the same patient or the same serum of the healthy person used in Example 5 was subjected to high-speed liquid chromatography while using the same apparatus as in Example 5 under the same conditions as in Example 5 except for using a mixture of acetonitrile and an aqueous 0.1% solution of sodium acetate (volume ratio of 11.25:88.75), a mixture of acetonitrile and an aqueous 0.3% solution of sodium acetate (volume ratio of 11.25:88.75), a mixture of acetonitrile and an aqueous 1.0% solution of sodium acetate (volume ratio of 11 25:88.75) or a mixture of acetonitrile and an aqueous 3.0% solution of sodium acetate instead of the mixture of acetonitrile and the aqueous solution of sodium acetate in Example 5.

The results are shown in FIGS. 4A to 4D, wherein each of the chromatograms of the healthy person's serum was piled on the corresponding chromatogram of the patient's serum.

As seen in the figures, while unusual peaks (blackened in the figures) are clearly seen in the chromatograms of the patient's serum, almost any one of such peak could not be seen in any one of chromatograms of the healthy person. In addition, it was found that the concentration of sodium acetate in the aqueous solution of the mixture may correlate to the number of peaks appearing in the chromatogram of the patient's serum.

EXAMPLE 7

The serum or the ascitic fluid obtained from a rat suffering from liver cirrhosis due to artificial inhalation of carbon tetrachloride for a long term was subjected to high-speed liquid chromatography in the same procedures and conditions in Example 6 except for using a mixture of acetonitrile and an aqueous 0.3% solution of sodium oxalate (volume ratio of 11.25:88.75) instead of the mixture of acetonitrile and the aqueous solution of sodium salt in Example 6.

As a result, two peaks were observed in both the chromatograms of the serum and of the ascitic fluid of the cirrhotic rat, which were almost the same as the peaks c and d in FIG. 3B.

However, no such peaks was seen in the chromatogram of normal rat's serum or ascitic fluid obtained by the same procedures in the present high speed liquid chromatography.

These findings suggest the probable use of the method according to the present invention in the test for evaluating the pharmaceutical effects while using experimental animals.

EXAMPLE 8

After having confirmed that the specific peak No. 3 appearing in the chromatogram of the patient's serum who was suffering from liver cirrhosis accompanying encephalosis in Example 1 according to the present invention also appears in every chromatogram of the respective sera of the three patients shown in Table 2 taken by the same procedures as in Example 1, the specific peak No. 3 was traced by the same techniques as in Example 1 on the three patients, respectively together with the tracing by biochemical examination, the results being shown also in Table 2.

TABLE 2

| Patient No. | Clinical finding | Intensity of Peak No. 3 | Value of biochemical analysis | |
|---|---|---|---|---|
| | | | GPT (KU) | GOT (KU) |
| No. 1 | degree of encephalosis, II | $9.3 \times 10^4$ | 112 | 52 |
| No. 2 | degree of ascites, ++ | $12.6 \times 10^4$ | 85 | 42 |
| No. 3 | degree of encephalosis, I and degree of ascites, ++ | $15.6 \times 10^4$ | 95 | 44 |

As seen in Table 2, while the index according to the present invention (the intensity of a specific peak in chromatogram prepared according to the present invention) corresponds very well to the clinical findings, the conventional value such as GPT and GOT do not necessarily correspond to the clinical findings.

From these findings, it is clear that the present invention is able to offer extremely precise informations concerning the presence or absence of the complication and the degree of seriousness of the disease in the patient suffering from hepatic disease(s).

EXAMPLE 9

Figure 5:
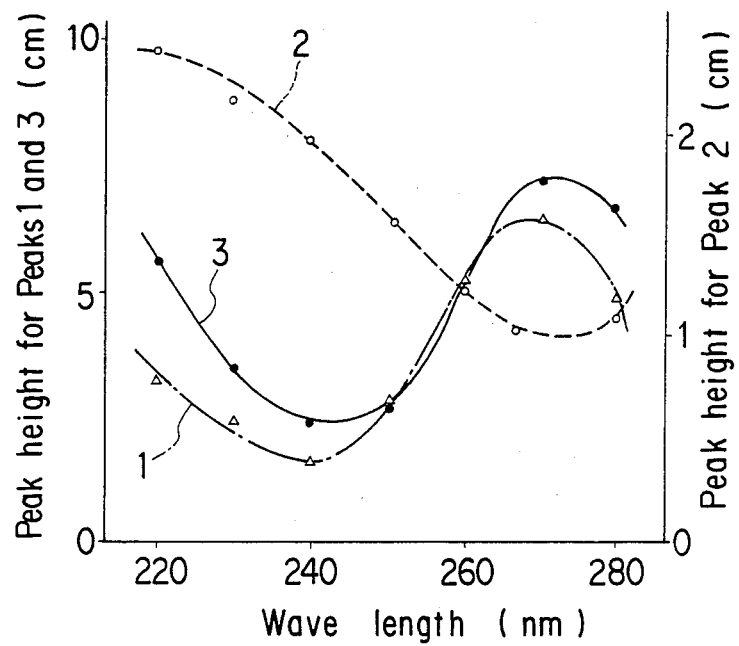
FIG. 5 shows the relationship of the height of the respective peaks in the chromatographic pattern to the wave length of UV-light used for detecting the peaks.

In Example 1, the height of the respective peaks appearing in the chromatogram of the patient according to the present invention was examined while changing the wave length of ultraviolet ray to 220, 230, 240, 250, 260 and 280 nm in UV detector of the high-speed liquid chromatographic apparatus in Example 1, the results are shown in FIG. 5.

As seen in FIG. 5, while the peak No. 1 and the peak No. 3 showed nearly the same tendency of height change corresponding to the change of wave length, only the peak No. 2 showed a different tendency of height change.

EXAMPLE 10

Figures 1, 8:
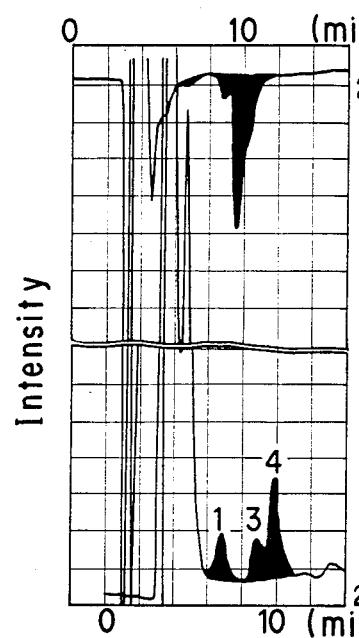
FIG. 6, FIGS. 8-1 to 8-10, FIGS. 9 to 15, FIG. 17 and FIG. 19 are the respective chromatographic pattern of the sera of various hepatic diseases
Figures 1, 8:
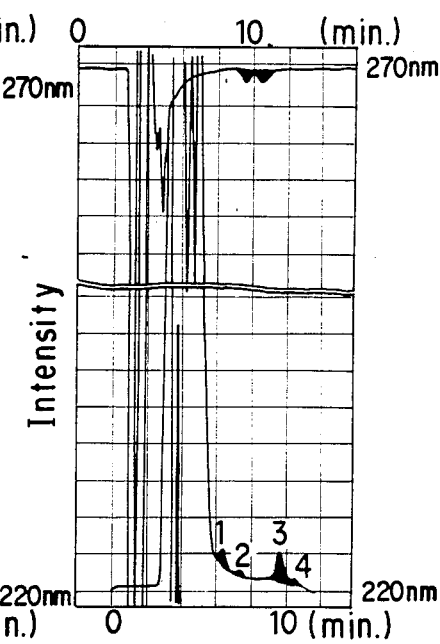
Figures 2, 8:
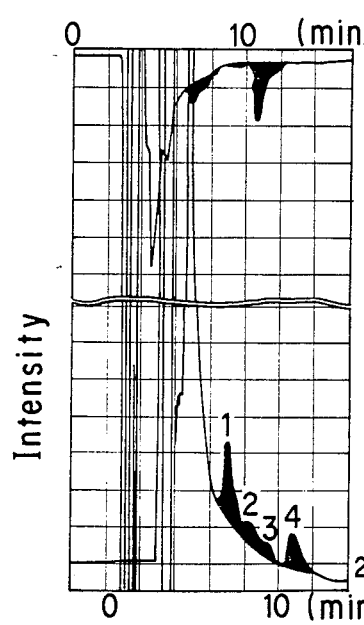
Figures 3, 8:
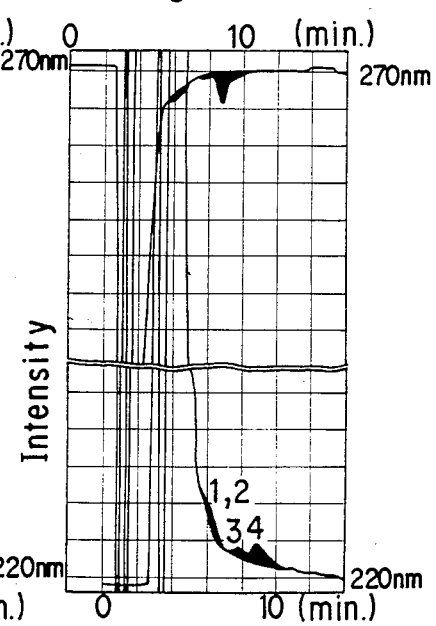
Figures 4, 8:
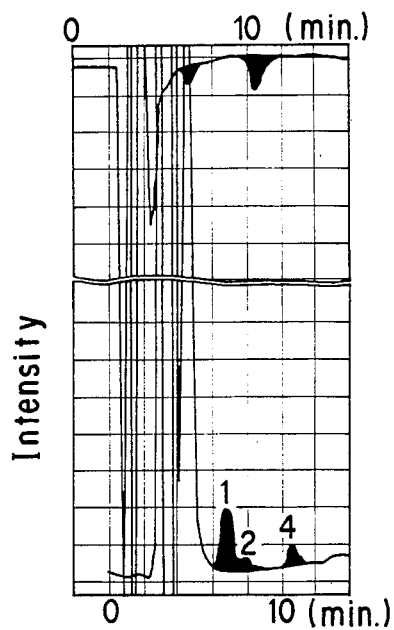
Figures 5, 8:
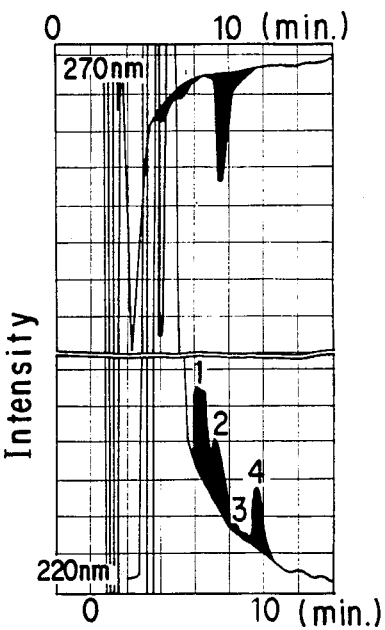
Figures 6, 8:
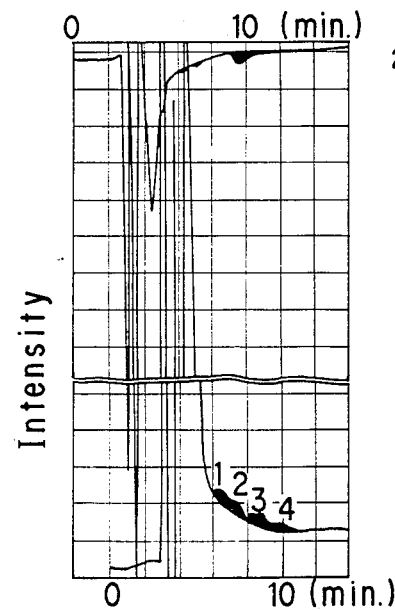
Figures 7, 8:
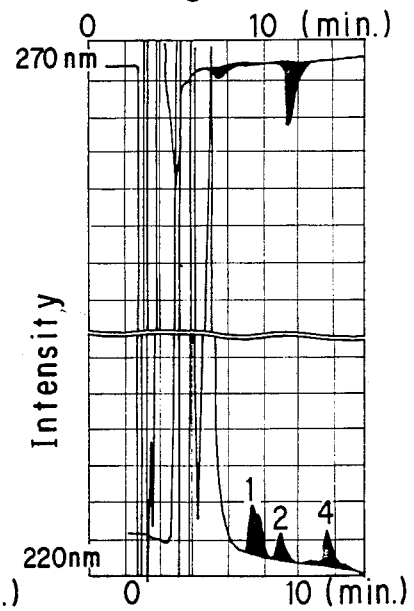
FIG. 7, FIG. 16 and FIG. 18 are the chromatographic pattern of the sera of healthy persons.

The serum of a healthy person or the serum of a patient suffering from cholestasis was treated as in Example 1 and subjected to the high-speed liquid chromatography as in Example 1 except for using a mixture of acetonitrile and an aqueous 3.0% solution of ammonium carbonate (volume ratio of 10:90) instead of the mixture of acetonitrile and the aqueous solution of sodium oxalate in Example 1 and pouring 20 microlitres of the de-proteinized specimen into the column, detection of the peaks being carried out while using two UV-lights, 220 and 270 nm in wave length simultaneously. As seen in FIGS. 6 and 7, while in the chromatogram of the patient's serum, four unusual peaks No. 1, No. 2, No. 3 and No. 4 were observed, none of such peaks could be observed in the chromatogram of the healthy person's serum.

These findings suggest that the morbid state of patients suffering from hepatic disease(s) will be judged by the analysis according to the method of the present invention.

EXAMPLE 11

Each of the sera obtained from 51 patients under the treatment for hepatic disease(s) was subjected to the analysis by the high-speed liquid chromatography according to the present invention under the same conditions as in Example 10. The results of the analysis are shown in Table 3, and the typical chromatographic patterns are shown in FIGS. 8-1 to 8-10.

As seen in Table 3, all the chromatographic patterns show the unusual peaks as are seen in FIGS. 8-1 to 8-10, which has never observed in the serum-chromatographic pattern of healthy persons.

TABLE 3

Relationship between the peaks in the high-speed liquid chromatographic pattern and the hepatic diseases

| Hepatic disease | Total number of patients | Number of patients showing Peaks of | | | |
|---|---|---|---|---|---|
| | | No. 1 | No. 2 | No. 3 | No. 4 |
| Acute hepatitis | 3 | 3 | 2 | 1 | 2 |
| Chronic hepatitis | 10 | 9 | 6 | 1 | 8 |
| Alcoholic hepatitis | 1 | 1 | 1 | 1 | 1 |
| Lupoid hepatitis | 1 | 1 | 1 | — | 1 |
| Liver cirrhosis | 20 | 18 | 17 | 4 | 18 |
| C* and hepatoma | 2 | 2 | 2 | — | 2 |
| C* and C.C** | 5 | 4 | 4 | 2 | 4 |
| C*, C.C** and hepatoma | 2 | 1 | 2 | 2 | 2 |
| (Cirrhosis total) | 29 | 25 | 25 | 8 | 26 |
| Primary biliary C* | 3 | 3 | 1 | — | 2 |
| Cholestasis | 3 | 3 | 1 | 3 | 3 |
| (grand total) | 50 | 45 | 37 | 14 | 43 |

Notes:
C* means liver cirrhosis
C.C** means encephalosis

EXAMPLE 12

The result of tracing the course of a woman of age of 44 diagnosed as acute hepatitis, chronic hepatitis and urticaria from the beginning of treatment as an outpatient, treatment as a hospitalized patient and de-hospitalization to treatment on relapse by the conventional biochemical examination and the method according to the present invention is shown in Table 4. In the method according to the present invention, the total area of the peaks Nos. 1 to 4 appearing in the high-speed liquid chromatographic pattern obtained by applying the same procedures as in Example 10 was used as the index.

By continued treatment, the values of biochemical examination gradually approached to the normal values and at the time of de-hospitalization (after 110 days of hospitalization), the values were in the normal range. On the other hand, the area of the specific peaks appearing in the chromatographic pattern showed a tendency of reducing slowly, however, the peaks are still remaining and since such peaks are not observed in the chromatographic pattern of the healthy person's serum, the thus obtained results suggest the necessity of continuing the treatment after her dehospitalization.

The above-mentioned situations tell that the method according to the present invention are able to watch the morbid state of hepatic diseases more precisely than the conventional biochemical methods for examination.

TABLE 4

| Treatment Course | | Biochemical Values | | | | Total peak area |
|---|---|---|---|---|---|---|
| | | GOT (KU) | GPT (KU) | LDH (IU/l) | γ-GTP (U/l) | |
| Yes | time of occurrence | 740 | 860 | 1198 | 1135 | — |
| " | 6 days after hospitalization | 340 | 669 | 474 | 198 | — |
| " | 19 days after hospitalization | 111 | 159 | 279 | 226 | $35.5 \times 10^4$ |
| " | 39 days after hospitalization | 69 | 78 | 288 | 124 | $5.4 \times 10^4$ |
| " | 65 days after hospitalization | 38 | 70 | 218 | 136 | $4.5 \times 10^4$ |
| " | 95 days after hospitalization | 26 | 28 | 262 | 82 | $3.0 \times 10^4$ |
| " | Time of dehospitalization (110 days) | 25 | 30 | 178 | 75 | $2.7 \times 10^4$ |
| No | 10 days after dehospitalization | 67 | 68 | 427 | 77 | $10.5 \times 10^4$ |
| " | 21 days after dehospitalization (relapse) | 76 | 97 | 620 | 158 | $25.1 \times 10^4$ |
| | Normal value | 8–40 | 5–35 | 50–400 | 0–60 | nearly zero |

EXAMPLE 13

Figures 8, 9:
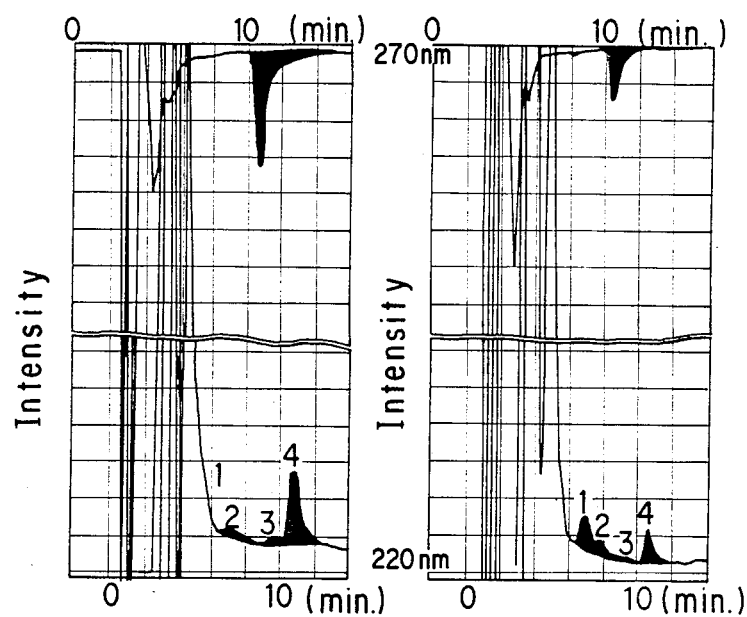

The same serum specimen was subjected to the high-speed liquid chromatography under the same conditions as in Example 10 except for using a mixture of acetonitrile and an aqueous 0.3% solution of ammonium carbonate (volume ratio of 8:92) instead of the mixture of acetonitrile and the aqueous solution in Example 10 to obtain a chromatographic pattern showing the specific unusual peaks as that shown in FIG. 9, which appeared after 7 min of the beginning of chromatography and did not appear in the chromatogram of the healthy person's serum. The same peaks were observed in the chromatograms of the patients respectively suffering from various liver diseases.

EXAMPLE 14

The same serum as in Example 10 was treated by another procedure of adding 500 microlitres of an aqueous 30% solution of trichloroacetic acid to 500 microlitres of the serum at a room temperature, subjecting the thus treated mixture to centrifuge, pouring 40 microlitres of the thus obtained supernatant liquid into the column. As a result, unusual peaks were observed in the chromatographic pattern, which have never been observed in the chromatographic pattern of the healthy person's serum.

In addition, the same serum taken from the patient was directly subjected without effecting de-proteinization to the high-speed chromatography as above.

In this case, also nearly the same peaks were observed in the chromatographic pattern.

EXAMPLE 15

A serum obtained from a patient suffering from acute liver failure was subjected to the high-speed liquid chromatography under the same conditions as those in Example 10 except for using a mixture of acetonitrile and an aqueous 0.3% solution of ammonium carbonate (volume ratio of 7.5:92.5), a mixture of acetonitrile and the aqueous 0.3% solution of ammonium carbonate (volume ratio of 15:85) or a mixture of acetonitrile and the aqueous 0.3% solution of ammonium carbonate (volume ratio of 25:75) instead of the mixture of acetonitrile and the aqueous solution in Example 10, while using a fluorescence monitor of λex of 220 nm and λem of larger than 340 nm.

Figures 8, 9, 10:
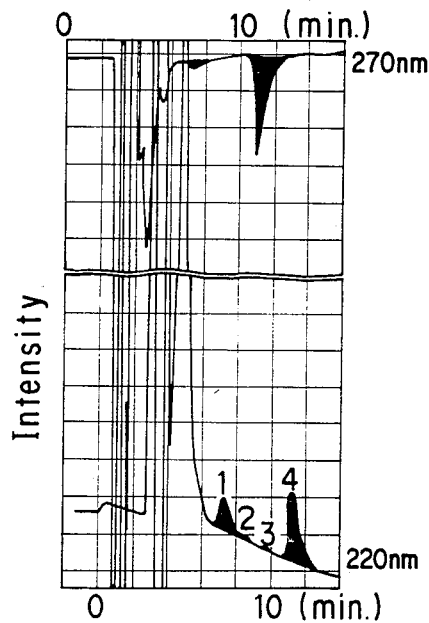
Figure 9:
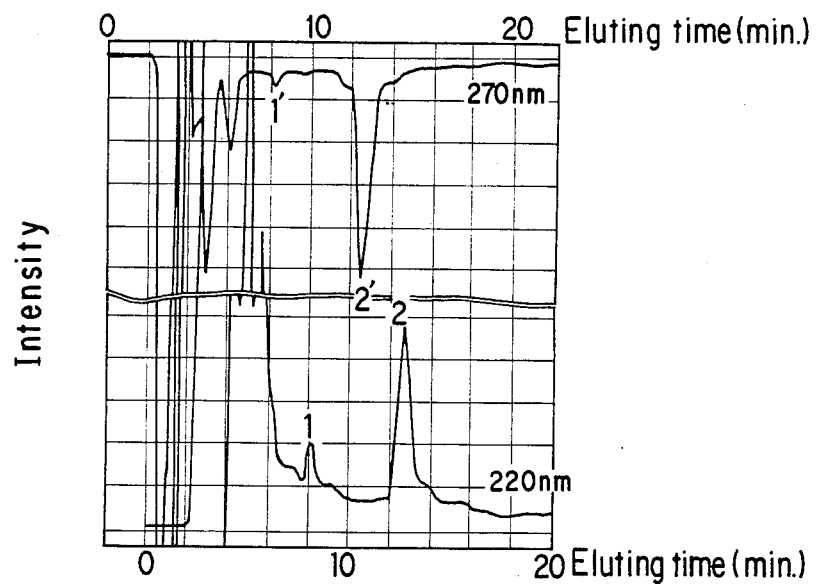
Figure 10:
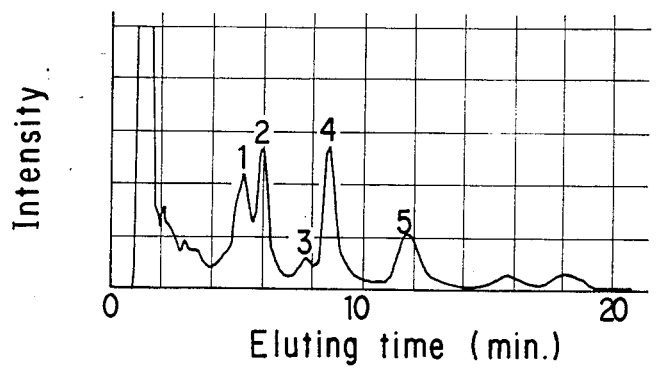
Figure 11:
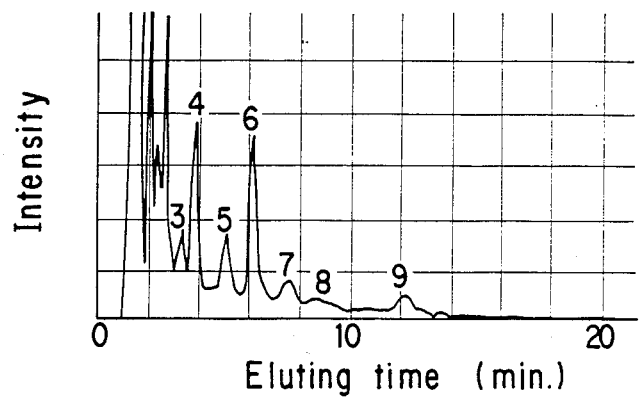
Figure 12:
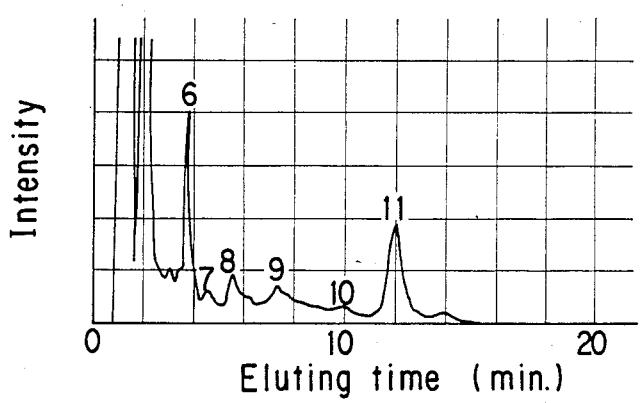

The results are respectively shown in FIG. 10 (the case of volume ratio of 7.5:92.5), FIG. 11 (the case of volume ratio of 15:85) and FIG. 12 (the case of volume ratio of 25:75).

As seen in the figures, the appearance and the number of the peaks depended on the volume ratio of acetonitrile to the aqueous solution of ammonium carbonate, however, such peak did not appear in the chromatographic pattern of the healthy person's serum.

EXAMPLE 16

The same procedures as in Example 13 were effected except for not carrying out the de-proteinizing of the serum and using the two columns connected in series. As a result, a peak corresponding to the peak No. 2 in FIG. 9 of Example 13 was clearly recognized in the chromatographic pattern of the present serum. On the other hand, in the chromatographic pattern obtained by subjecting the not-deprotenized serum of a healthy person to the same high-speed liquid chromatographic apparatus, no such peak was recognized.

COMPARATIVE EXAMPLE 1

For the sake of comparison, the same serum of the patient suffering from cholestasis in Example 10 was pre-treated as in Example 10 and subsequently subjected to the high-speed liquid chromatography while using two columns connected in series and packed with a carrier (HG-3011, made by HITACHI Works) and a phosphoric acid buffer solution of pH of 7.4 as the eluent instead of the mixture of acetonitrile and the aqueous solution of ammonium carbonate in Example 10, under the same conditions as in Example 10. As a result, no unusual peak other than those of uric acid and creatinine could be detected in the chromatographic pattern.

EXAMPLE 17

A serum taken from a patient suffering from liver cirrhosis was subjected to the same high-speed liquid chromatography as in Example 10 except for using a mixture of acetonitrile and an aqueous 0.3% ammonium carbonate (volume ratio of 10:90) instead of the mixture of acetonitrile and the aqueous solution in Example 10.

Figure 13:
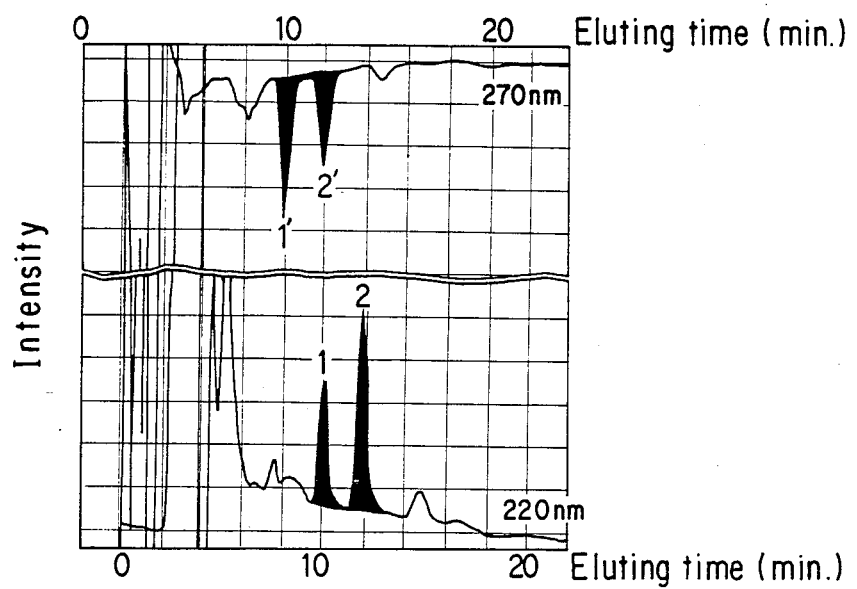

As a result, a chromatographic pattern shown in FIG. 13 was obtained and four unusual peaks, Nos. 1, 1', 2 and 2' were recognized therein. In the chromatographic pattern obtained from the serum of a healthy person, such peak was not detected.

EXAMPLE 18

Each one of sera obtained from four patients suffering from alcoholic fatty liver was subjected to the same high-speed liquid chromatography as in Example 17. The results are shown in Table 5 together with the values of biochemical examination of the same serum.

From Table 5, it is recognized that the area of the peaks appearing in the chromatographic pattern increases with the aggravation of the morbid state of the liver disease, and that the method according to the present invention is applicable to clinical examination of the patients suffering from hepatic disease(s).

TABLE 5

| | Specimen from Patients Nos. | | | |
|---|---|---|---|---|
| Item | 1 | 2 | 3 | 4 |
| GOT(KU) | 62 | 44 | 40 | 123 |
| GPT(KU) | 63 | 58 | 69 | 287 |
| Alkali-phosphatase | 7.5 | 9.8 | 10.2 | 12.9 |
| γ-GTP (U/liter) | 45 | 138 | 123 | 693 |
| T.S.BA* (micromol/liter) | 1.1 | 1.3 | 2.7 | 336 |
| GCA** (micromol/liter) | 0 | 0 | 0 | 44 |
| Area of Peak No. 1'*** | 1.8 | 1.9 | 1.5 | 12.5 |
| Area of Peak No. 2'*** | 3.65 | 3.5 | 5.1 | 30.6 |

Note:
***Peaks Nos. 1' and 2' appearing in the chromatographic pattern of the respective sera from the patient, the peak being detected by UV of 270 nm and the area being divided by $10^5$.
T.S.BA*: total serum bile acid
GCA**: glycocholic acid.

EXAMPLE 19

Serum speicmens were obtained from a patient suffering from chronic renal failure complicated with hepatitis, repsectively, before treatment (refer to FIG. 14) and after 2 month-treatment (refer to FIG. 15), and subjected to the hgih-speepd liquid chromatography according to Example 10 under the same conditions as in Example 13.

Figure 14:
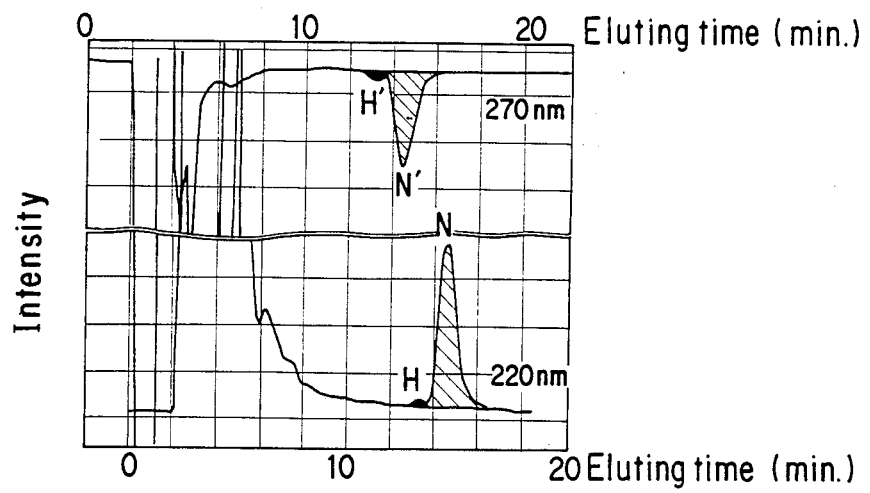
Figure 15:
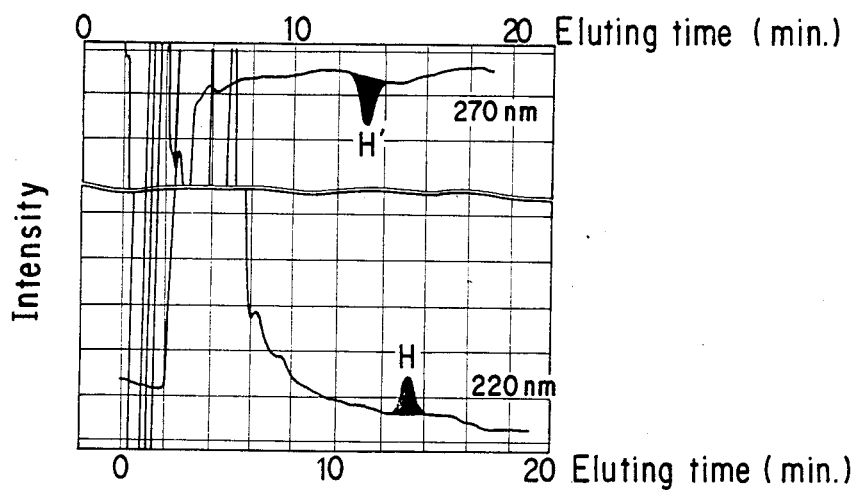

The results are shown in FIGS. 14 and 15, wherein the peaks N and N' are recognized to be due to kidney failure and the area thereof clearly shows the reduction after treatment. In addition, the peaks H and H' are due to hepatitis, and no improvement due to the treatment was recognized.

For reference, the values of biochemical examination before and after treatment are shown below:

| | Creatinine (mg/dl) | BUN (mg/dl) | GOT (KU) | Amount of dairy urine (ml) |
|---|---|---|---|---|
| Before treatment | 14 | 160 | 40 | 600 |
| After treatment | 10 | 120 | 45 | 1200 |

EXAMPLE 20

Figure 16:
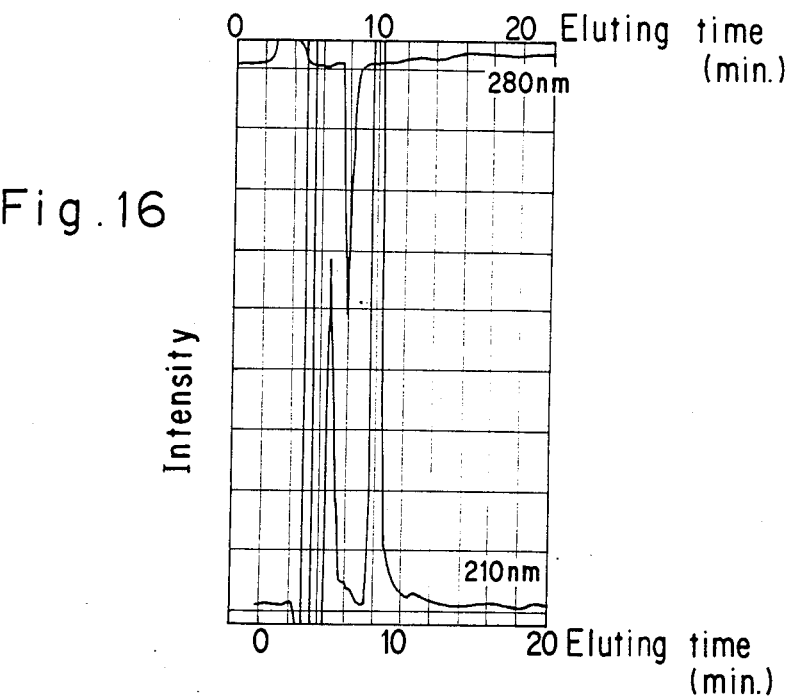
Figure 17:
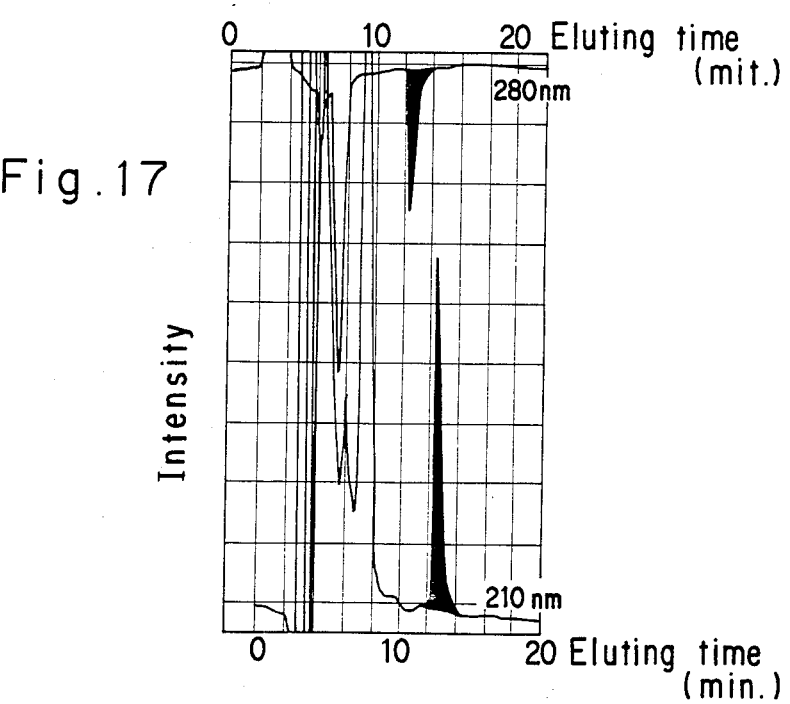

Each of the two serum specimens used in Example 1 was treated by the same procedures as in Example 10 and subsequently subjected to the high-speed liquid chromatography under the same conditions as in Example 10 except for using a mixture of acetonitrile and an aqueous 0.1% solution of acetic acid (volume ratio of 10:90) and further using UV-lights of 210 and 280 nm at a sensitivity of 0.02 instead of the mixture of acetonitrile and an aqueous solution of ammonium carbonate and of UV-lights of 220 and 270 nm at a sensitivity of 0.04 in Example 10. Of the thus obtained two chromatographic patterns within 20 min (refer to FIGS. 16 and 17), the one taken on the patient's serum showed unusual peak (refer to FIG. 2) which was not detected in the pattern on the healthy person's serum (refer to FIG. 16).

EXAMPLE 21

Figure 18:
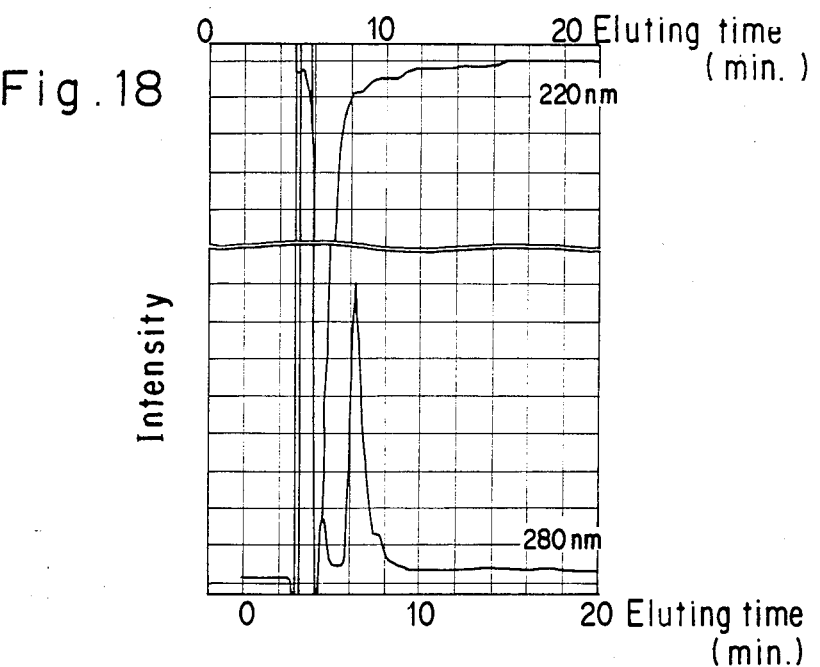
Figure 19:
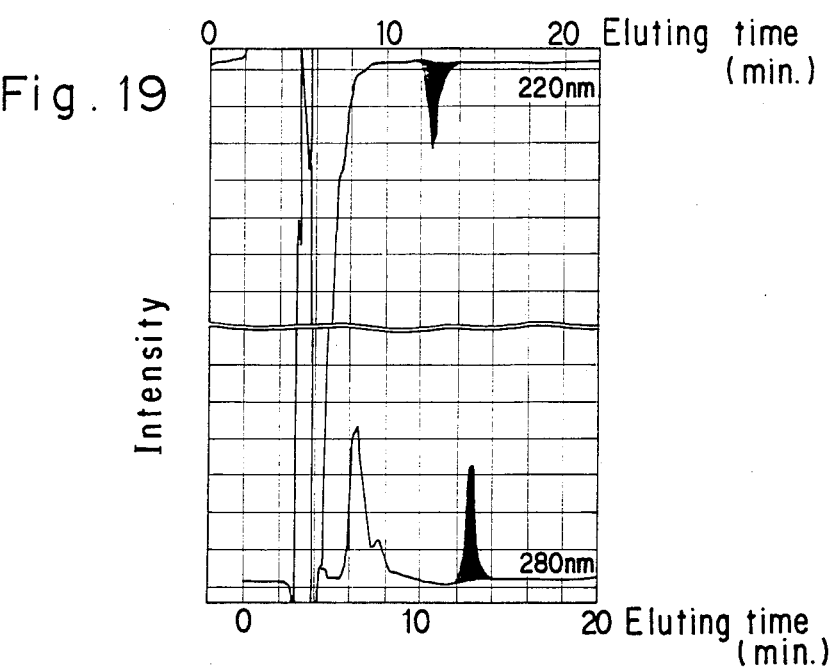

Each one of the two serum specimens, respectively obtained from a patient suffering from liver cirrhosis accompanying encephalosis and a healthy person was pre-treated by the precedures of de-proteinization shown in Example 10 and subsequently subjected to chromatography under the same conditions as in Example 10 except for using a mixture of acetonitrile and an aqueous 0.01% solution of acetic acid (volume ratio of 10:90) under UV-lights of 220 nm at a sensitivity of 0.04 and 280 nm at a sensitivity of 0.02 instead of the mixture of acetonitrile and the aqueous solution under UV-lights of 220 nm at a sensitivity of 0.04 and 270 nm at a sensitivity of 0.04 to obtain the two chromatographic patterns (refer to FIGS. 18 and 19) within 20 min. In the chromatographic pattern (FIG. 19) taken on the patient's serum, an unusual peak was recognized, which was not recognizable in the chromatographic pattern taken on the healthy person's serum.

EXAMPLE 22

Serum specimens were obtained from a patient suffering from a complication of liver cirrhosis, hepatoma and encephalosis corresponding to the aggravation of his morbid state and after treating the specimen for de-proteinization as in Example 1, the thus treated specimen was subjected to high-speed liquid chromatography under the same conditions as in Example 10. The results are shown in Table 6 together with the values obtained by the conventional biochemical examination for reference. As seen in Table 6, in spite of the aggravation of the patient's morbid state from the degree of encephalosis of I to the degree of II, the values of biochemical examination did not show any remarkable change except for the value of $NH_3$. On the other hand, the area of the peaks appearing in the chromatographic patterns on the patient's serum accurately reflects the change of the morbid state, and the applicability of the method according to the present invention has been thus elucidated.

TABLE 6

| | Serum taken at Stage of | | |
|---|---|---|---|
| Item(unit) | Deg. encephalosis[1] I | II | Normal value |
| GOT (KU) | 67 | 68 | 8–40 |
| GPT (KU) | 36 | 32 | 5–35 |
| Alkali Phos.[2](U) | 22.6 | 25.9 | 2.7–10.0 |
| γ-GTP (u/liter) | 24 | 12 | 0–60 |
| T-chol.[3] (mg/dl) | 111 | 61 | 130–230 |
| LDH (IU/liter) | 340 | 330 | 50–400 |
| $NH_3$ (mcG/dl) | 124 | 251 | 0–120 |
| BUN (mg/dl) | 17 | 14 | 10–20 |
| Area of the peak(s) in the serum detected by the present invention under UV of 280 nm | $7.5 \times 10^4$ | $12.5 \times 10^4$ | nearly 0 |

Notes:
[1]Degree of encephalosis
[2]Alkali phosphatase
[3]total cholesterol.

EXAMPLE 23

Figure 20A:
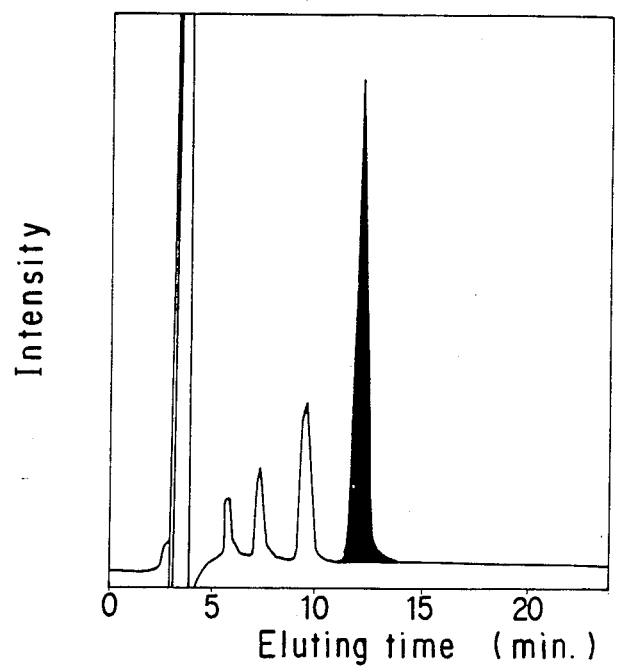
Figure 20B:
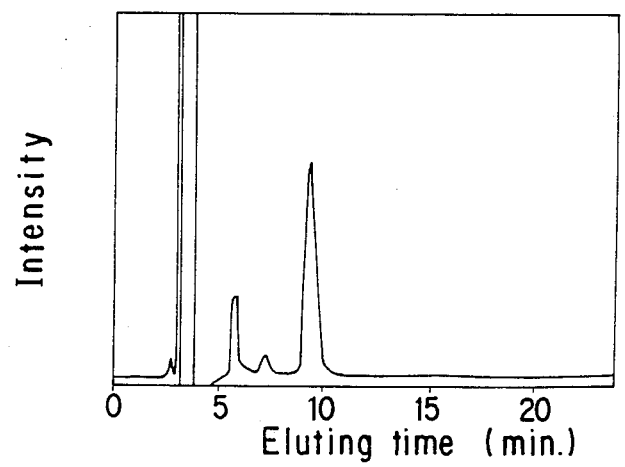

Each one of the serum specimens, respectively obtained from a patient suffering from liver cirrhosis with encephalosis and from a healthy person was de-proteinized as in Example 1 and subsequently subjected to the high-speed liquid chromatography under the same conditions as in Example 1 except for using a mixture of acetonitrile and an aqueous 0.1% solution of citric acid (volume ratio of 10:90) instead of the mixture of acetonitrile and the aqueous solution in Example 1 to obtain the two chromatographic patterns within min, one of which corresponds to the patient (FIG. 20A), and the other of which corresponds to the healthy person (FIG. 20B). As seen in FIGS. 20A and 20B, an unusual peak was detected in the patient's serum, which was not recognized in the healthy person's serum.

EXAMPLE 24

Each one of the two plasmic specimens, respectively obtained from a patient suffering from cholestasis and from a healthy person was pre-treated by the same procedures as in Example 1 and subsequently subjected to high-speed liquid chromatography under the same conditions as in Example 1 except for using a mixture of acetonitrile and an aqueous 0.1% solution of oxalic acid or succinic acid (volume ratio of 10:90) instead of the mixture of acetonitrile and the aqueous solution in Example 1.

As the result, an unusual peak appeared in the chromatographic pattern on the patient's plasma regardless of the kinds of the solute in the aqueous solution (oxalic acid and succinic acid). However, such a peak was not detected in the pattern on the healthy person's plasma.

EXAMPLE 25

Each one of the same serum specimens as in Example 23 were treated by the same procedures as in Example 1 except for using a mixture of acetonitrile and an aqueous 0.5% solution of citric acid (volume ratio of 10:90) instead of the mixture of acetonitrile and the aqueous solution in Example 1 to obtain the two chromatographic patterns, of which the one corresponding to the serum of the patient showed an unusual peak which was not present in the pattern corresponding to the healthy person.

EXAMPLE 26

Each one of the serum specimens, respectively obtained from a patient suffering from acute liver failure and from a healthy person was treated as in Example 1 except for using a mixture of acetonitrile and an aqueous 0.1% solution of citric acid (volume ratio of 8:92, 12:88 or 15:85) under the same conditions as in Example 1 to obtain six chromatographic patterns of the respective serum specimens. As the result, an unusual peak was observed in the respective chromatographic patterns on the serum of the patient, however, such a peak was not detected in the three chromatographic patterns on the healthy person's serum.

EXAMPLE 27

The high-speed liquid chromatography in Example 1 was applied to the serum specimen obtained from a patient suffering from a complication of liver cirrhosis and hepatoma to whom encephalosis was recognized, for tracing the patient's morbid state.

The results are shown in Table 7 together with the values of biochemical examination on the patient.

TABLE 7

| Item | (unit) | Specimen taken in Stage A | Stage B | Normal value |
|---|---|---|---|---|
| GOT | (KU) | 67 | 68 | 8–40 |
| GPT | (KU) | 36 | 32 | 5–35 |
| alkali phosphatase | (U) | 22.6 | 25.9 | 2.7–10.0 |
| $\gamma$-GTP | (u/liter) | 24 | 12 | 0–60 |
| LDH | (IU/liter) | 340 | 330 | 50–400 |
| T-cholesterol | (mg/dl) | 111 | 61 | 130–230 |
| $NH_3$ | (mcG/dl) | 124 | 251 | 0–120 |
| BUN | (mg/dl) | 17 | 14 | 10–20 |
| Area of Peak detected by 270 nm | | $4.87 \times 10^4$ | $6.28 \times 10^4$ | nearly 0 |
| Clinical finding on the degree of encephalosis | | I | II | — |

EXAMPLE 28

The morbid state of a hospitalized patient suffering from liver cirrhosis and being under treatment was traced by using the specified peak appearing in the chromatographic pattern obtained by the same procedures as in Example 23 and in addition by using the values of biochemical examination. The results are shown in Table 8 as follows:

TABLE 8

| Clinical finding | Intensity of the peak (count $\times 10^4$) | Biochemical value GPT (KU) | GOT (KU) |
|---|---|---|---|
| Degree of encephalosis II | 7.5 | 112 | 52 |
| Degree of cholestasis++ | 9.98 | 85 | 42 |
| Degree of encephalosis I plus Degree of cholestasis++ | 13.9 | 95 | 44 |

As seen in Table 8, the findings by the present invention corresponds favorably to the clinical findings, however, the conventional values of biochemical examination did not necessarily correspond to the clinical findings. These results clearly indicate that the present invention is able to supply an extremely precise information concerning the seriousness in a patient of a hepatic disease and the presence and absence of the complication in a hepatic disease.

What is claimed is:

1. A method for detecting a specific liquid chromatography peak or a specific liquid chromatography peak pattern correlating to the morbid state of a hepatic disease, comprising: subjecting a specimen of plasma, serum, cerebrospinal fluid, lymph, ascitic fluid, bile or urine obtained from a human living body or a de-proteinized specimen to liquid chromatography, and using as an eluent a mixture of acetonitrile and an aqueous solution of at least one member selected from the group consisting of acetic acid, polybasic organic acids, salts or organic acids and ammonium carbonate, at a volume ratio of said acetonitrile to said aqueous solution of 5:95 to 15:85, wherein the said peak or peak pattern can be detected within 30 minutes.

2. The method of claim 1, comprising using as the said polybasic organic acid oxalic acid, succinic acid or citric acid.

3. The method of claim 1, comprising using as the said salts or oganic acids a sodium salt, a potassium salt, a magnesium salt or an ammonium salt of an organic acid selected from the group consisting of formic acid, acetic acid, propionic acid, oxalic acid, succinic acid and citric acid.

4. The method of claim 1, comprising using a concentration of acetic acid in the said aqueous solution of from 0.1 to 0.5% by weight.

5. The method of claim 1, comprising using a concentration of ammonium carbonate in the said aqueous solution of from 0.3 to 3.0% by weight.

6. The method of claim 1, comprising using a concentration of polybasic organic acid in the said aqueous soltuion of from 0.1 to 0.5% by weight.

7. The method of claim 1, comprising using a concentration of salt or organic acid in the said aqueous solution of from 0.1 to 5.0% by weight.

* * * * *